(12) United States Patent
Dumont

(10) Patent No.: US 10,315,179 B2
(45) Date of Patent: Jun. 11, 2019

(54) RADIOSYNTHESISER ADD-ON DEVICE

(71) Applicant: GE Healthcare Limited, Buckinghamshire (GB)

(72) Inventor: Philippe Dumont, Loncin (BE)

(73) Assignee: GE HEALTHCARE LIMITED, Buckinghamshire (GB)

( * ) Notice: Subject to any disclaimer, the term of this patent is extended or adjusted under 35 U.S.C. 154(b) by 17 days.

(21) Appl. No.: 15/546,988

(22) PCT Filed: Mar. 16, 2016

(86) PCT No.: PCT/EP2016/055694
§ 371 (c)(1),
(2) Date: Jul. 27, 2017

(87) PCT Pub. No.: WO2016/146686
PCT Pub. Date: Sep. 22, 2016

(65) Prior Publication Data
US 2018/0008950 A1 Jan. 11, 2018

(30) Foreign Application Priority Data
Mar. 16, 2015 (GB) .................................. 1504407.6

(51) Int. Cl.
*B01J 19/00* (2006.01)
*C07B 59/00* (2006.01)

(52) U.S. Cl.
CPC ......... *B01J 19/004* (2013.01); *B01J 19/0093* (2013.01); *C07B 59/00* (2013.01); *B01J 2219/00058* (2013.01); *B01J 2219/00799* (2013.01); *B01J 2219/00833* (2013.01); *B01J 2219/00867* (2013.01); *B01J 2219/00894* (2013.01); *B01J 2219/00918* (2013.01); *B01J 2219/00927* (2013.01);
(Continued)

(58) Field of Classification Search
CPC ...... B01J 19/00; B01J 19/0006; B01J 19/004; B01J 19/24; B01J 2219/00049–2219/00058; B01J 2219/24; C07B 59/00; C07B 2200/05
See application file for complete search history.

(56) References Cited

U.S. PATENT DOCUMENTS

| 7,235,216 B2 * | 6/2007 | Kiselev | ..................... A61J 3/00 422/159 |
|---|---|---|---|
| 2006/0245980 A1 | 11/2006 | Kiselev et al. | |
| 2018/0021750 A1 * | 1/2018 | Dumont | ............... B01J 19/0093 |

FOREIGN PATENT DOCUMENTS

| WO | 2012170602 A1 | 12/2012 | |
| WO | WO-2013012813 A1 * | 1/2013 | .......... B01J 19/0093 |

(Continued)

OTHER PUBLICATIONS

International Search Report and the Written Opinion of the International Searching Authority, or the Declaration from International Appl. No. PCT/EP2016/055694, dated Jul. 12, 2016.
(Continued)

*Primary Examiner* — Natasha E Young
(74) *Attorney, Agent, or Firm* — Arent Fox LLP

(57) ABSTRACT

The present invention relates to an automated radiosynthesis device adapted for the addition of multiple additional components. The automated radiosynthesis device of the invention enables a wider range of radiochemical synthetic processes to be carried out in an automated fashion.

20 Claims, 6 Drawing Sheets

(52) U.S. Cl.
CPC .......... *B01J 2219/00952* (2013.01); *B01J 2219/00961* (2013.01); *B01J 2219/00986* (2013.01); *C07B 2200/05* (2013.01)

(56) References Cited

FOREIGN PATENT DOCUMENTS

| WO | 2013049608 A2 | 4/2013 |
| WO | 2014194576 A1 | 12/2014 |
| WO | 2016146686 A1 | 9/2016 |

OTHER PUBLICATIONS

Great Britain Search Report from GB Appl. No. GB1504407.6, dated Aug. 17, 2015.

* cited by examiner

RADIOSYNTHESISER ADD-ON DEVICE

This application is a national stage application claiming priority to PCT/EP2016/055694, published as WO 2016/146686 and filed on Mar. 16, 2016, which claims priority to Great Britain Patent Application Serial No. GB 1504407.6, filed on Mar. 16, 2015.

TECHNICAL FIELD OF THE INVENTION

The present invention relates to the synthesis of radiolabelled compounds. In particular, the present invention relates to an apparatus for the automated synthesis of radiolabelled compounds, especially radiotracer compounds.

DESCRIPTION OF RELATED ART

Radiolabelled compounds for use as in vivo imaging agents are currently typically prepared by means of an automated synthesis apparatus (alternatively "radiosynthesizer"). Such automated synthesis apparatuses are commercially available from a range of suppliers, including: GE Healthcare; CTI Inc.; Ion Beam Applications S.A. (Chemin du Cyclotron 3, B-1348 Louvain-La-Neuve, Belgium); Raytest (Germany) and Bioscan (USA). The radiochemistry takes place in a "cassette" or "cartridge" designed to fit removably and interchangeably onto the apparatus, in such a way that mechanical movement of moving parts of the apparatus controls the operation of the cassette. Suitable cassettes may be provided as a kit of parts that is assembled onto the apparatus in a number of steps, or may be provided as a single piece that is attached in a single step, thereby reducing the risk of human error. The single piece arrangement is generally a disposable single use cassette which comprises all the reagents, reaction vessels and apparatus necessary to carry out the preparation of a given batch of radiopharmaceutical.

It is desirable that the synthesizer is flexible enough to accommodate the needs of different chemistries and that the system can evolve to accommodate future needs.

SUMMARY OF THE INVENTION

The present invention provides an automated radiosynthesis device (1) comprising:
(i) a plurality of connectors (2) for removably attaching a disposable kit (3);
(ii) a plurality of actuators (4a-i) to selectively control moving parts of said disposable kit (3);
(iii) a control unit (5) for directing the selective control of the moving parts of said disposable kit (3) by said plurality of actuators (4a-i);
(iv) a reaction vessel heating well (6);
(v) an inert gas conduit (7);
(vi) a vacuum conduit (8);
(vii) a radioisotope conduit (9);
(viii) means (10) to fix add-on devices (11) onto the radiosynthesis device (1) at various locations.

The device of the invention provides enhanced flexibility in the automated synthesis of different radioactive tracers, or multiple runs of the same radioactive tracer. Known automated radiosynthesis devices can be readily adapted to comprise the features of the present invention allowing the user to greatly expand the capabilities of these devices in a straightforward manner.

BRIEF DESCRIPTION OF THE FIGURES

In FIG. 1 a T-shaped rail on the front of the cassette drawer holds in place reaction vessel heating wells (6) comprised within add-on devices (11).

DETAILED DESCRIPTION OF THE PREFERRED EMBODIMENTS

Figure 1:
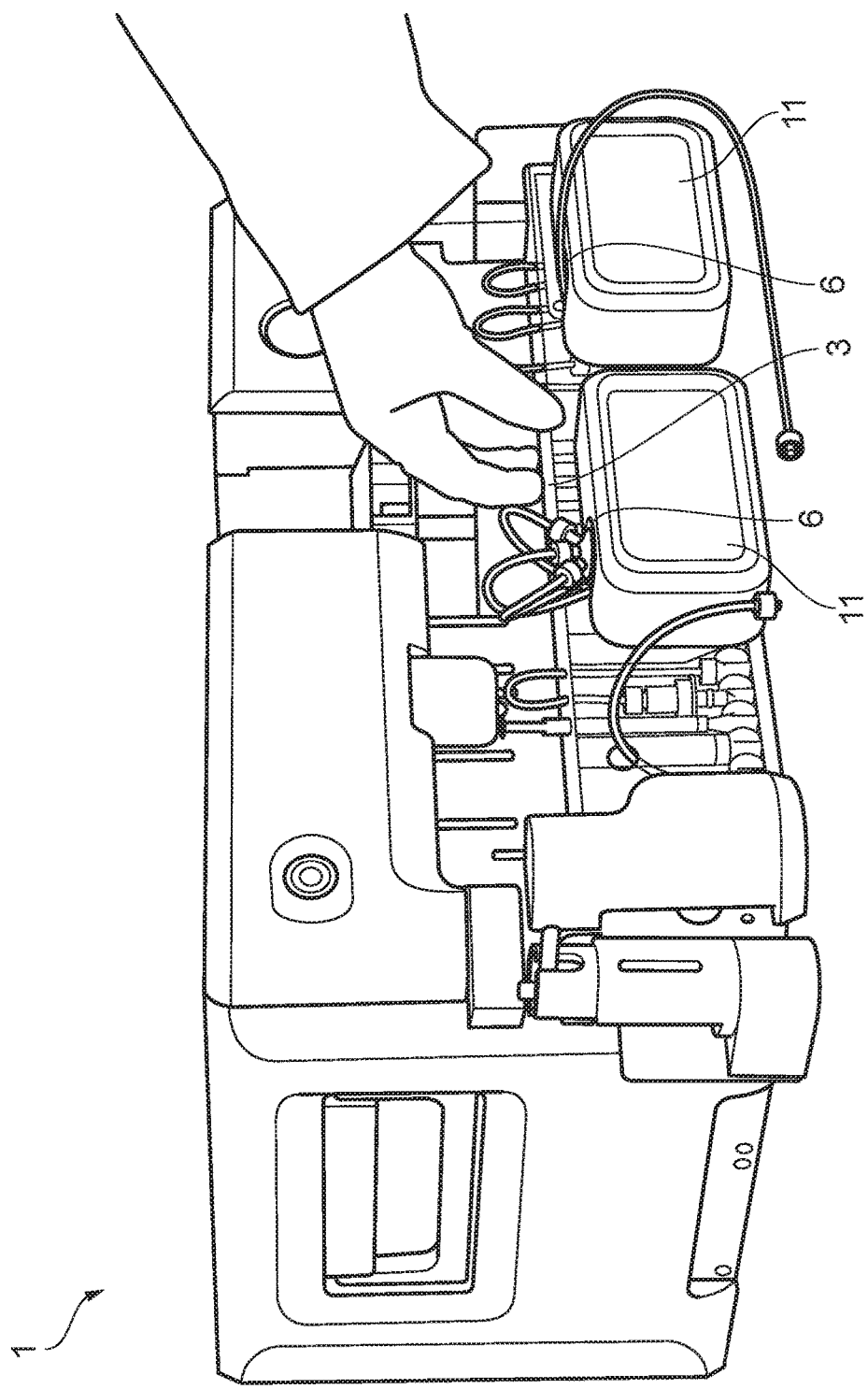
FIG. 1 shows an exemplary automated radiosynthesis device of the invention where a cassette is being inserted into a cassette drawer.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "automated radiosynthesis device" (also referred to herein as "radiosynthesis device") as used herein refers to an automated module based on the principle of unit operations as described by Satyamurthy et al (1999 Clin Positr Imag; 2(5): 233-253). The term "unit operations" means that complex processes are reduced to a series of simple operations or reactions, which can be applied to a range of materials. Such automated radiosynthesisers are commercially available from a range of suppliers (Satyamurthy et al, above), including: GE Healthcare; CTI Inc; Ion Beam Applications S.A. (Chemin du Cyclotron 3, B-1348 Louvain-La-Neuve, Belgium); Raytest (Germany) and Bioscan (USA). Automated radiosynthesis devices are designed to be employed in a suitably configured radioactive work cell, or "hot cell", which provides suitable radiation shielding to protect the operator from potential radiation dose, as well as ventilation to remove chemical and/or radioactive vapours. Using a cassette the automated radiosynthesis device has the flexibility to make a variety of different radiopharmaceuticals with minimal risk of cross-contamination, by simply changing the cassette. This approach also has the advantages of simplified set-up hence reduced risk of operator error, improved GMP (good manufacturing practice) compliance, multi-tracer capability, rapid change between production runs, pre-run automated diagnostic checking of the cassette and reagents, automated cross-check (e.g. using a barcode or radio-frequency identification) of chemical reagents vs. the synthesis to be carried out, reagent traceability, single-use and hence no risk of cross-contamination, tamper and abuse resistance. The radiosynthesis device is programmed to operate pumps, syringes, valves, heating element, and controls the provision of nitrogen and application of vacuum to the disposable kit so as to direct the source fluid into mixing with the reagents, performing the chemical reactions, through the appropriate purification cartridges, and selectively pumping the output tracer and waste fluids into appropriate vial receptacles outside the disposable kit. While the fluid collected in the output vial is typically input into another system for either purification and/or dispensement, the radiosynthesis device and disposable kit can also be connected to a separate purification system which returns a purified compound back to the disposable kit for further processing.

Each of the "connectors" of the automated radiosynthesis device of the present invention represents one half of a pair of mating connectors or fasteners where the other half is present at a corresponding location on the disposable kit. In one embodiment of the automated radiosynthesis device of the invention said plurality of connectors is selected from the group comprising fasteners and fluidic connectors. In one embodiment of the automated radiosynthesis device of the invention said fluidic connectors are selected from the group comprising push-on type connectors, luer slip connectors or luer screw connectors.

The term "disposable kit" herein refers either to a kit of parts or to a cassette. A "kit of parts" comprises first and second end valves and a plurality of interior valves oriented along a flowpath therebetween. Such a kit includes a reaction vessel adapted to be connected to one or more of the valves, at least one pump means supported on a valve, at least one reagent vial holding contents which are directable into the flowpath, wherein the reagent vial adapted to be connected to said flowpath so that the contents may be directed into the flowpath. The kit further includes at least one cartridge adapted to be connected across at least one of the valves. The components of the kit of parts are provided separately and it is required that the user assemble them prior to use. In contrast, a "cassette" is a pre-assembled single-use piece of apparatus designed to fit removably and interchangeably onto an automated radiosynthesiser. A typical cassette has an elongate manifold including first and second end valves and a plurality of interior valves oriented along a manifold flowpath therebetween. The manifold defines an elongate manifold flowpath between each of the valves. The cassette includes a reaction vessel, at least one pump means (e.g. a syringe) supported on a valve, at least one reagent vial holding contents which are directable into the manifold flowpath, and at least one purification cartridge connected across at least one of the valves. The cassette is desirably adaptable for synthesizing clinical batches of different radiopharmaceuticals with minimal customer installation and connections. Connections between the cassette and the radiosynthesis device in one embodiment are automatically made to the reagent vials by driving the septums thereof onto penetrating spikes of the cassette so as to allow the synthesizer access to use the reagents.

In one embodiment of the automated radiosynthesis device of the invention said disposable kit is suitable for the synthesis of a radiotracer compound. A "radiotracer compound" is a biologically active chemical compound in which one or more atoms have been replaced by a radioisotope. Radiotracer compounds can be formulated for use in nuclear medicine, including single photon emission computed tomography (SPECT), positron emission tomography (PET) and scintigraphy. Such radiotracer compounds are well-known to those of skill in the art. The reader is referred for example to "Radiochemical Syntheses: Radiopharmaceuticals for Positron Emission Tomography" (Volume 1, 2001, Wiley, Scott & Hockley, Eds.) and to "Handbook of Radiopharmaceuticals: Radiochemistry and Applications" (2003, Wiley, Welch & Redvanly, Eds.) for discussion of the common general knowledge in the art of radiopharmaceuticals. In one embodiment said radiotracer compound is a PET tracer. In one embodiment said radiotracer compound is an $^{18}$F-labelled PET tracer. An "[$^{18}$F]-labelled PET tracer" is a chemical compound that comprises an $^{18}$F atom and is suitable for use as a PET tracer. Non-limiting examples of [$^{18}$F]-labelled PET tracers include [$^{18}$F]fluorodeoxyglucose ([$^{18}$F]FDG), [$^{18}$F]Fluoromisonidazole ([$^{18}$F]FMISO), [$^{18}$F]fluorothymidine ([$^{18}$F]FLT), [$^{18}$F]Fluoroazomycin arabinofuranoside ([$^{18}$F]FAZA), [$^{18}$F]Fluoroethyl-choline ([$^{18}$F]FECH), [$^{18}$F]fluorocyclobutane-1-carboxylic acid ([$^{18}$F]FACBC), [$^{18}$F]flumanezil ([$^{18}$F]FMZ), [$^{18}$F]tyrosine, [$^{18}$F]altanaserine, 4-[$^{18}$F]fluoro-3-iodobenzyl guanidine ([$^{18}$F]FIBG), meta-[$^{18}$F]fluorobenzylguanidine ([$^{18}$F]mFBG) and [$^{18}$F]5-fluorouracil.

The term "actuators" refers to any suitable means to move or control parts of the disposable kit. An actuator is operated by a source of energy, typically electric current, hydraulic fluid pressure, or pneumatic pressure, and converts that energy into motion. In one embodiment of the automated radiosynthesis device of the present invention said plurality of actuators is selected from the group comprising rotatable arms for stopcocks of valves, linear actuators, arms that press onto reagent vials and pinch valves (e.g. solenoid pinch valves selectively blocking flow).

The term "moving parts" refers to those parts of the disposable kit that move in a controlled fashion by means of co-operative functional association with actuators on the radiosynthesis device. In one embodiment of the automated radiosynthesis device of the invention said moving parts of said disposable kit are selected from the group comprising reagent vials, syringes and valves.

The "control unit" of the radiosynthesis device of the present invention includes software for operating the disposable kit in accordance with a particular radiosynthesis method. The software comprises instructions for a particular radiosynthesis method to be carried out on said disposable kit attached to said automated radiosynthesis device. The software is provided as a non-transitory computer readable storage medium with an executable program for performing a particular radiosynthesis method when the appropriate disposable kit is mounted to radiosynthesis device.

The "reaction vessel heating well" of the radiosynthesis device of the invention is designed to receive a reaction vessel provided as part of the disposable kit so as to provide any heat required for chemical reactions occurring therein.

The "inert gas conduit", "vacuum conduit" and "radioisotope conduit" are suitably tubing linking the radiosynthesis device in a fluid-tight manner respectively to a source of inert gas (e.g. nitrogen), a vacuum (e.g. a pump) and a source of a radioisotope (e.g. a vial or the output line of a cyclotron). The conduits can comprise spigots to permit controlled delivery. The inert gas and vacuum assist in fluid transfer through the manifold and in operation of the disposable kit. The radioisotope conduit may extend from the source of the radioisotope to a delivery plunger.

The "means to fix add-on devices" is a support or scaffold onto which devices required for a particular radiosynthesis method can be mounted. The devices are suitably positioned to be able to function alongside the disposable kit.

In one embodiment of the automated radiosynthesis device of the present invention said means to fix add-on devices is a rail. In one embodiment said rail is a T-shaped rail. In one embodiment said add-on devices are connected by T-shaped nut.

In one embodiment of the automated radiosynthesis device of the present invention said reaction vessel heating well is fixed to said means to fix add-on devices.

In one embodiment said means to fix add-on devices is part of a cassette drawer of the radiosynthesis device. The "cassette drawer" is the means used to interface a cassette with the radiosynthesis device. The operator inserts a cassette into a drawer and connection of the cassette to the radiosynthesis device is achieved by movement of the drawer towards the radiosynthesis device. FIG. 1 illustrates insertion of a cassette (3) into such a drawer. In FIG. 1 a T-shaped rail located on the front of the cassette drawer (rail not visible in FIG. 1) holds the 2 reaction vessel heating wells (6) comprised in the add-on devices (11) in place.

Figure 2:
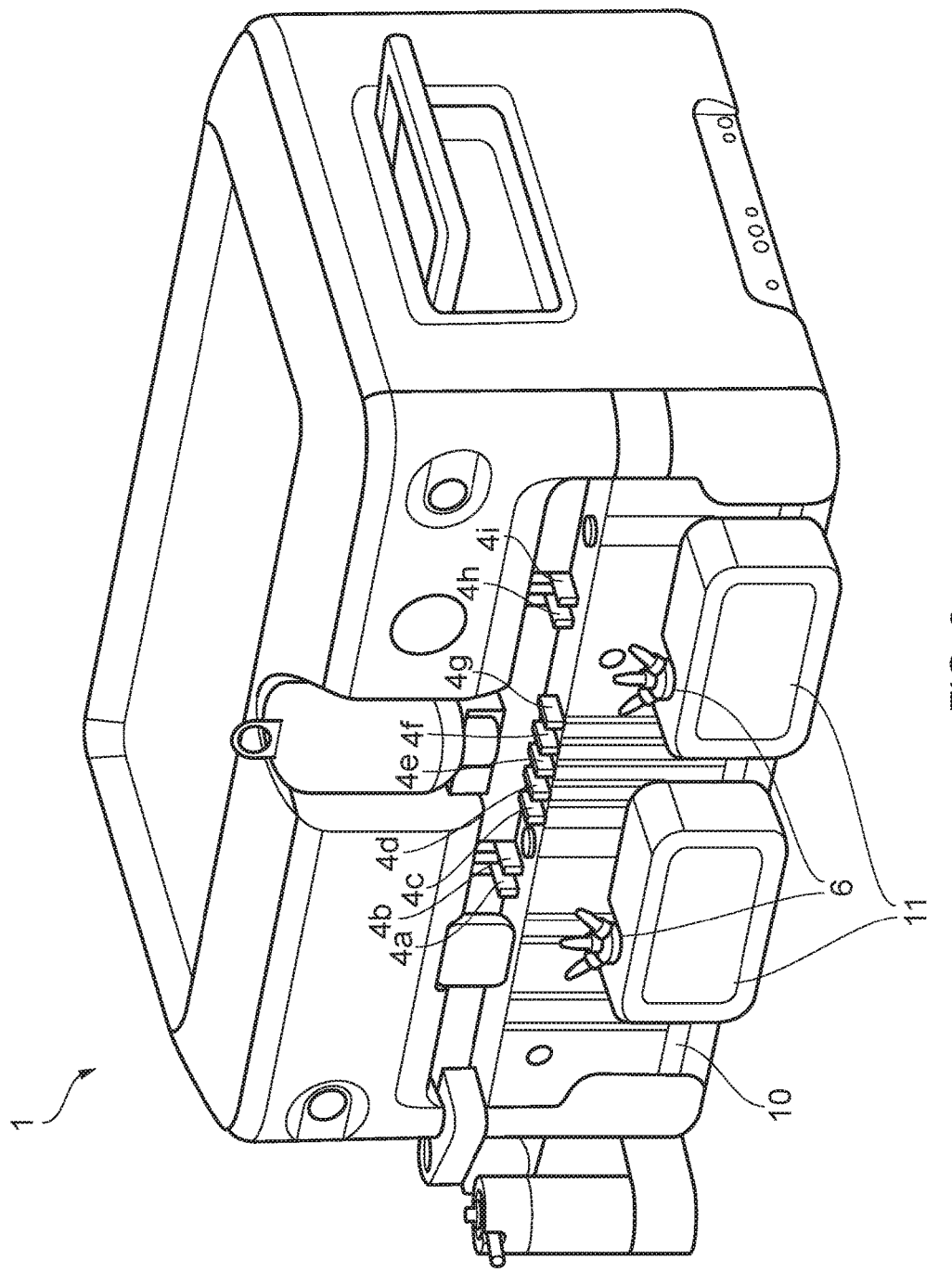
FIG. 2 shows the same exemplary radiosynthesis device as illustrated in FIG. 1 from the opposite side showing a series of actuators (4a-i). Actuators 4a and 4b work in concert, as do actuators 4c-g and actuators 4h and 4i.

FIG. 2 is another view of the same exemplary radiosynthesis device as illustrated in FIG. 1. In this embodiment the rail is T-shaped (10) and the reaction vessel heaters (6) are mounted onto the rail by means of T-nuts (according to DIN 508 standard).

Figure 3:
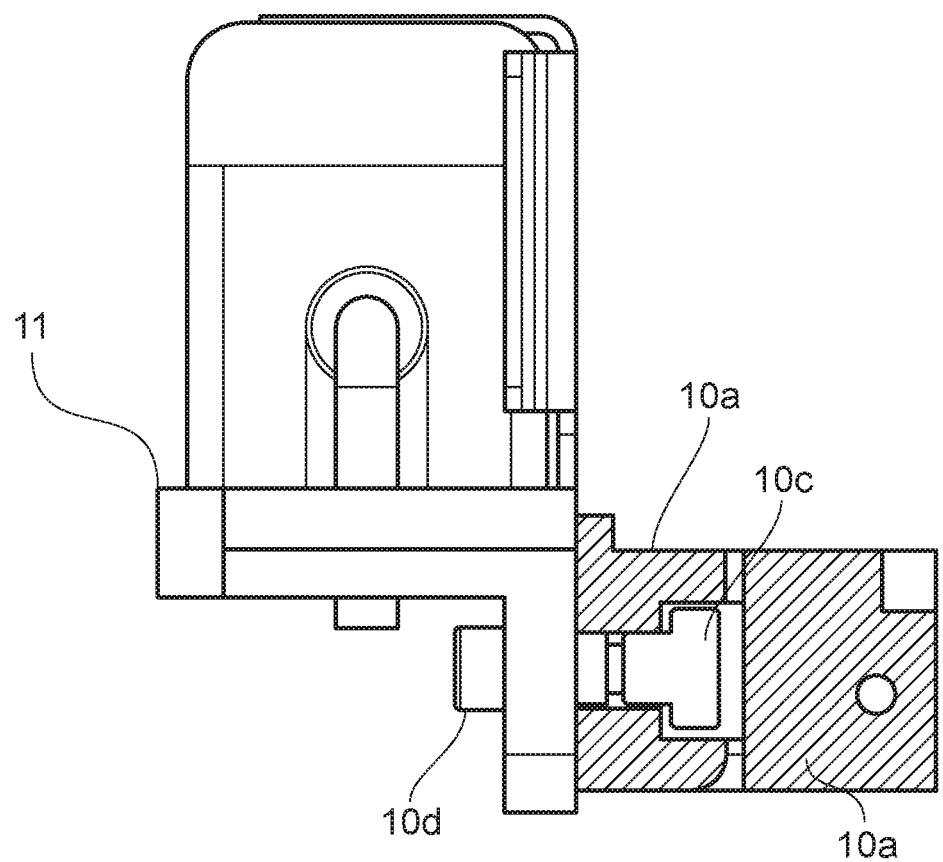
FIGS. 3 and 4 show cross-sectional views of an exemplary add-on device (11) fixed onto a T-shaped rail (10a) using a screw (10d) and a T-shaped nut (10c).
Figure 4:
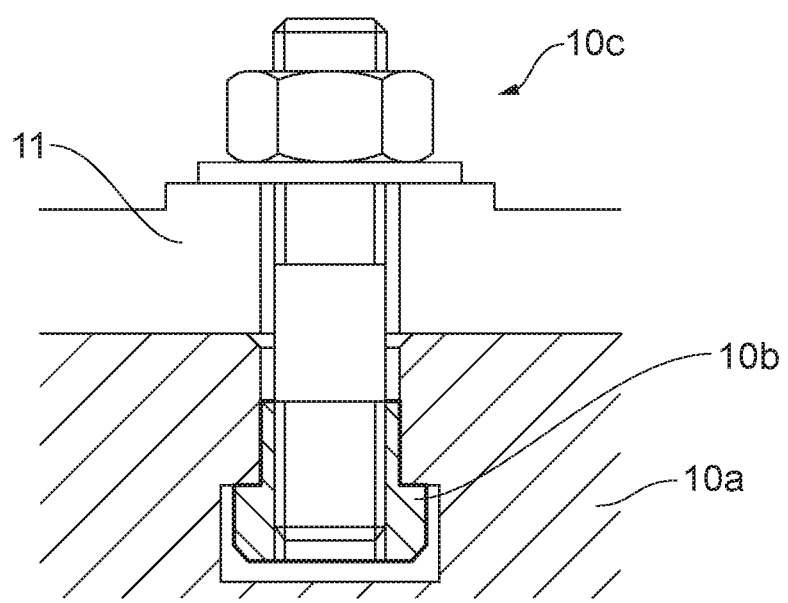

Cross-sectional views of exemplary add-on devices (11) fixed onto a T-shaped rail (10a) using a screw (10d) and a T-shaped nut (10c) are illustrated in FIGS. 3 and 4. In FIG. 3 the add-on device (11) comprises a reaction vessel heating well and in FIG. 4 the add-on device (11) is more generic. FIGS. 3 and 4 show that the arrangement is secured with a screw (10d).

Figure 5:
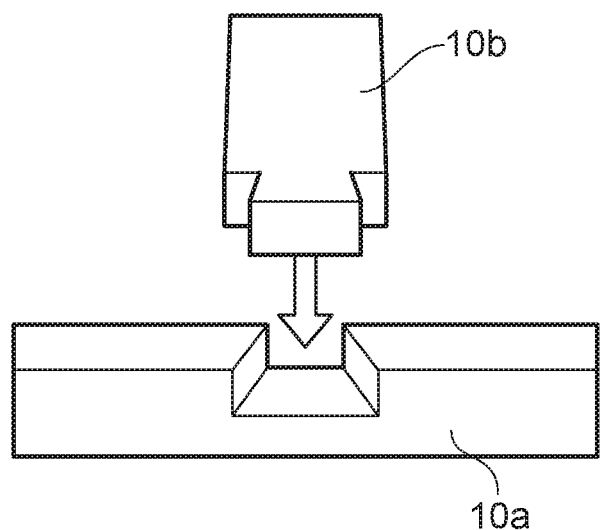
FIGS. 5 and 6 illustrate other exemplary configurations for the means (10) to fix add-on devices where the design of the rail (10a) and the nut (10b) are of different shapes.
Figure 6:
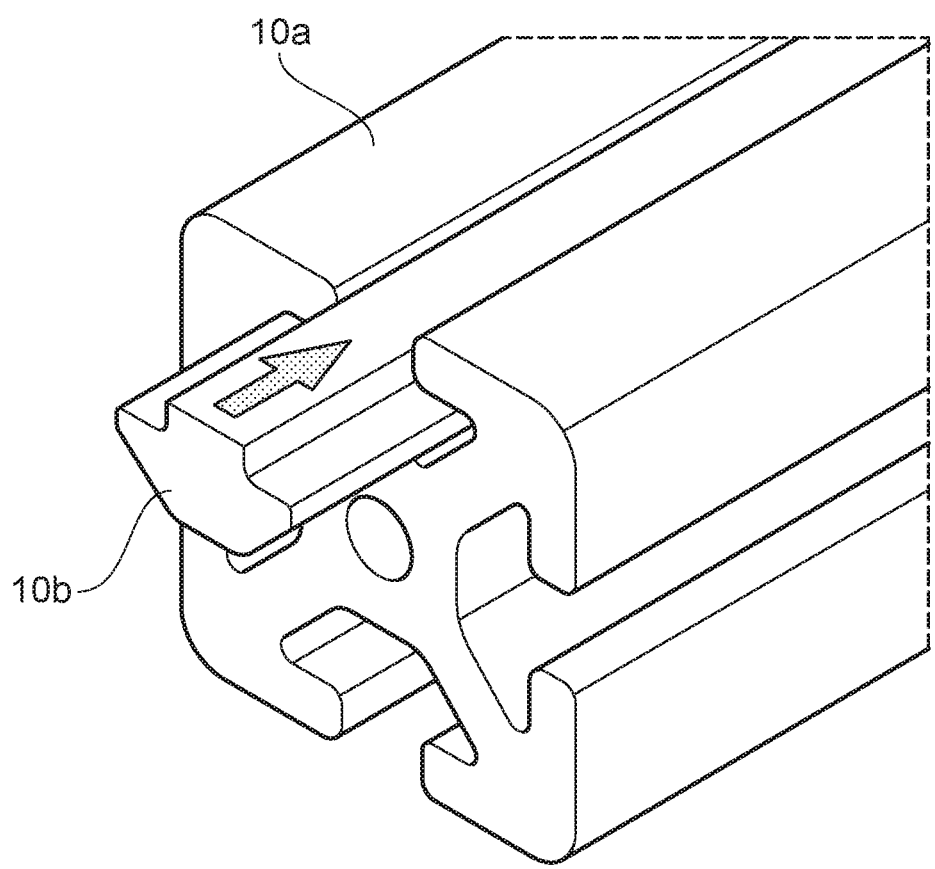

Other configurations are also envisaged for the means to fix add-on devices. For example, in certain embodiments the design of the rail (10a) and the nut (10b) could be of different shapes as illustrated in FIGS. 5 and 6.

It is also envisaged that a variety of add-on devices can be attached. In one embodiment of the present invention said add-on devices comprise:
an additional reaction vessel heating well, useful for carrying out processes with multiple chemical reactions;
a radioactivity detector for improving in-process control by measuring radioactivity at critical location;
a temperature sensor to monitor and control temperature at critical location;
a vial holder for additional reagents enabling to add more vials with chemicals;
a solid-phase extraction (SPE) cartridge heating or cooling device enabling more complex chemistries requiring temperature control on solid phase extraction cartridges;
additional actuators to extend the disposable kit operation capability; and,
a web cam enabling to watch the process, which can be of interest during the development phase.

Features, integers, characteristics, compounds, chemical moieties or groups described in conjunction with a particular aspect, embodiment or example of the invention are to be understood to be applicable to any other aspect, embodiment or example described herein unless incompatible therewith.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. An automated radiosynthesis device comprising:
   (i) a plurality of connectors for removably attaching a disposable kit;
   (ii) a plurality of actuators to selectively control moving parts of said disposable kit;
   (iii) a control unit for directing the selective control of the moving parts of said disposable kit by said plurality of actuators;
   (iv) a reaction vessel heating well;
   (v) an inert gas conduit;
   (vi) a vacuum conduit;
   (vii) a radioisotope conduit;
   (viii) means to fix add-on devices onto the radiosynthesis device at various locations, wherein said means to fix add-on devices comprises a rail and means for securing said add-on devices to said rail.

2. The device of claim 1, wherein said connectors are selected from fasteners and/or fluidic connectors.

3. The device as device of claim 2, wherein said fluidic connectors are selected from push-on type connectors, luer slip connectors and/or luer screw connectors.

4. The device of claim 1, wherein said disposable kit is suitable for the synthesis of a radiotracer compound.

5. The device of claim 4, wherein said radiotracer compound is a positron-emission tomography (PET) tracer.

6. The device of claim 5, wherein said radiotracer compound is an $^{18}$F-labelled PET tracer.

7. The device of claim 1, wherein said disposable kit is a single-use cassette.

8. The device of claim 1, wherein said plurality of actuators is selected from rotatable arms for stopcocks of valves, linear actuators, arms that press onto reagent vials and/or pinch valves.

9. The device of claim 1, wherein said moving parts of said disposable kit are selected from the reagent vials, syringes and/or valves.

10. The device of claim 1, wherein said control unit includes software comprising instructions for a particular radiosynthesis method to be carried out on said disposable kit attached to said automated radiosynthesis device.

11. The device of claim 1, wherein said reaction vessel heating well is fixed to said means to fix add-on devices.

12. The device of claim 1, wherein said means to fix add-on devices is part of a cassette drawer of the radiosynthesis device.

13. The device of claim 1, wherein said rail is a T-shaped rail.

14. The device of claim 1, wherein said means for securing said devices to said rail comprises a T-shaped nut and associated screw.

15. The device of claim 1, wherein said add-on devices are selected from:
   an additional reaction vessel heating well;
   a radioactivity detector;
   a temperature sensor;
   a vial holder for additional reagents;
   a solid-phase extraction (SPE) cartridge heating or cooling device;
   additional actuators to extend the disposable kit operation capability; and/or, a web cam.

16. An automated radiosynthesis device comprising:
   (i) a plurality of connectors for removably attaching a disposable kit;

(ii) a plurality of actuators to selectively control moving parts of said disposable kit;
(iii) a control unit for directing the selective control of the moving parts of said disposable kit by said plurality of actuators;
(iv) a reaction vessel heating well;
(v) an inert gas conduit;
(vi) a vacuum conduit;
(vii) a radioisotope conduit;
(viii) means to fix add-on devices onto the radiosynthesis device at various locations,
   wherein said means to fix add-on devices is part of a cassette drawer of the radiosynthesis device comprises a T-shaped rail and means for securing said add-on devices to said T-shaped rail,
   wherein said means for securing said devices to said rail comprises a T-shaped nut and associated screw, and
   wherein said reaction vessel heating well is fixed to said means to fix add-on devices.

17. The device of claim 16, wherein said plurality of connectors is selected from fasteners and/or fluidic connectors, said fluidic connectors are selected from the group comprising push-on type connectors, luer slip connectors or luer screw connectors, and/or said disposable kit is a single-use cassette suitable for the synthesis of a radiotracer compound.

18. The device of claim 17, wherein said radiotracer compound is a $^{18}$F-labelled positron-emission tomography (PET) tracer.

19. The device of claim 16, wherein said plurality of actuators is selected from rotatable arms for stopcocks of valves, linear actuators, arms that press onto reagent vials and/or pinch valves, said moving parts of said disposable kit are selected from reagent vials, syringes and valves, and/or said control unit includes software comprising instructions for a particular radiosynthesis method to be carried out on said disposable kit attached to said automated radiosynthesis device.

20. The device of claim 16, wherein said add-on devices are selected from:
   an additional reaction vessel heating well;
   a radioactivity detector;
   a temperature sensor;
   a vial holder for additional reagents;
   a solid-phase extraction (SPE) cartridge heating or cooling device;
   additional actuators to extend the disposable kit operation capability; and/or, a web cam.

* * * * *